United States Patent [19]

Masilamani et al.

[11] Patent Number: 5,136,033
[45] Date of Patent: Aug. 4, 1992

[54] ION SELECTIVE FLUOROGENIC REAGENTS

[75] Inventors: Divakaran Masilamani, Morristown; Mariann E. Lucas, Netcong; George S. Hammond, Madison, all of N.J.

[73] Assignee: Allied-Signal Inc., Morris Township, Morris County, N.J.

[21] Appl. No.: 88,370

[22] Filed: Aug. 24, 1987

[51] Int. Cl.$^5$ .................. C07D 419/02; C07D 321/00; G01N 33/20

[52] U.S. Cl. ...................... 540/468; 540/469; 540/472; 549/200; 549/348; 549/349; 549/350; 549/351; 549/352; 436/74

[58] Field of Search ...................... 436/73, 74, 79, 172, 436/805, 74; 422/50, 55, 56; 540/450, 460, 467, 468, 469; 549/200, 348, 349, 350, 351, 352

[56] References Cited

U.S. PATENT DOCUMENTS 4,631,119  12/1986  Gokel et al. .................. 204/59 R
4,645,744   2/1987  Charlton ...................... 436/74

FOREIGN PATENT DOCUMENTS 51946     5/1982  European Pat. Off. .
62207267  6/1986  Japan .

OTHER PUBLICATIONS

H. G. Lohr et al "Chromo and Fluoroinophores . . . " Acct. Chem. Res. 18 65–72 (1985).
Nishida et al "Fluorescent Crown Ether . . . " Chem. Lett. pp. 1853–1854 (1982).
Takagi et al "Crown Compounds . . . " Topic Curr. Chem. 121 39–65 (1984).
Merck index p. 1247.
K. W. Street, Jr., et al. "A New Metal Sensitive Fluorescence Reagent" Analytical Ltrs, 19(7 and 8), 735–745 (1986).
A. P. de Silva "Fluorescent Signalling Crown Ethers; 'Switching On' of . . . " J. Chem. Soc. Chem. Commun. 1986, pp. 1709–1710.
S. Fujine et al. "Lithium Isotope Separation by Displacement Chromo . . . " Jrnl of Nuclear Science and Techn. 20(5), pp. 439–440 (May 1983).
J. P. Konopelski et al. "Synthesis, Cation Binding, and Photophysical Prop . . . " J. Chem. Soc. Chem. Commun., 1985, pp. 433–435.

*Primary Examiner*—C. Warren Ivy
*Assistant Examiner*—Celia Chang
*Attorney, Agent, or Firm*—D. L. Webster; G. H. Fuchs; R. C. Stewart, II

[57] ABSTRACT

Novel fluorogenic ionophores have been synthesized which selectively bind ions such as potassium and sodium, even in neutral aqueous and alcoholic media and respond to such binding by fluorescence quenching or enhancement. These ionophores are ideal for the selective and direct determination of ions in biological or environmental samples and the like. The ionophores are also suitable for incorporation into fiber optic-based sensors for the continuous in vivo or in vitro monitoring of metal ions in blood or other biological fluids.

14 Claims, 8 Drawing Sheets

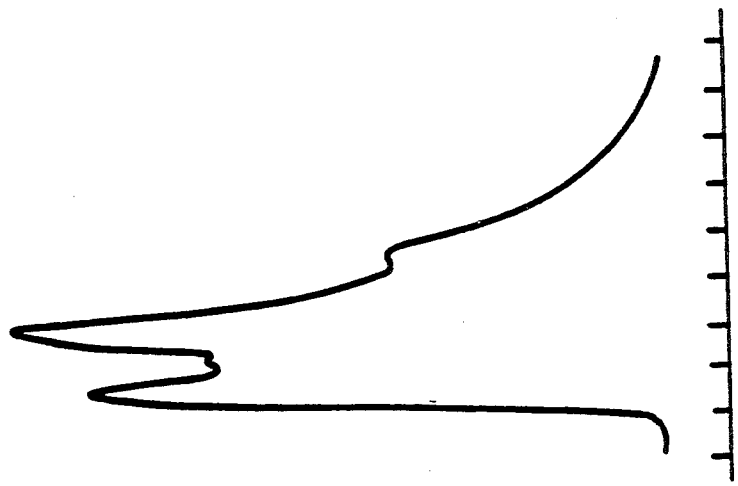
10⁻⁵ M in Dioxane
EX 309 nm  slit 10 nm
EM 320–420 nm  slit 1 nm
FIGURE 8(b)
FIGURE 8(a)

ION SELECTIVE FLUOROGENIC REAGENTS

FIELD OF THE INVENTION

Novel fluorogenic ionophores have been synthesized which selectively bind ions such as potassium and sodium, even in neutral aqueous and alcoholic media and respond to such binding by fluorescence quenching or enhancement. These ionophores are ideal for the selective and direct determination of ions in biological or environmental samples and the like. The ionophores are also suitable for incorporation into fiber optic-based sensors for the continuous in vivo or in vitro monitoring of metal ions in blood or other biological fluids.

BACKGROUND OF THE INVENTION

The measurement of fluorescence quenching or enhanced fluorescence emission when metal ions are bound to these fluorogenic ionophores is more accurate than measurements based on chromogenic phenomena. This is because fluorescence measurements are made against a dark background, whereas chromogenic methods require detection of absorption maxima or changes in absorption coefficients. Among the fluorogenic ionophores reported in the literature are those described by Nishida, et al. "Fluorescent Crown Ether Reagent For Alkali and Alkaline Earth Metal Ions," *Chem. Lett.*, pp. 1853–1854, (1982), by Kenneth W. Street, Jr. and Shelly A. Kraus in "A New Metal Sensitive Fluorescence Reagent," *Anal. Lett.*, 19 (7 and 8), 735–745 (1986), and by A. P. deSilva et al., "Fluorescent Signaling Crown Ethers: 'Switching On' of Fluorescence by Alkali Metal Ion Recognition and Binding in situ" *J. Chem. Soc., Chem. Commun.* 1986, 1709–10. However, all the above ionophores suffer from a disadvantage in that they are pH dependent, and can function only at a pH much higher than that of normal body fluid, and hence cannot be used for in vivo applications.

SUMMARY OF THE INVENTION

The present invention provides a novel ionophore comprising an "ion-recognizing system" fused to a "signal moiety" through one or more heteroatoms having a non-bonded electron pair, said ionophore having the General Structural Formula:

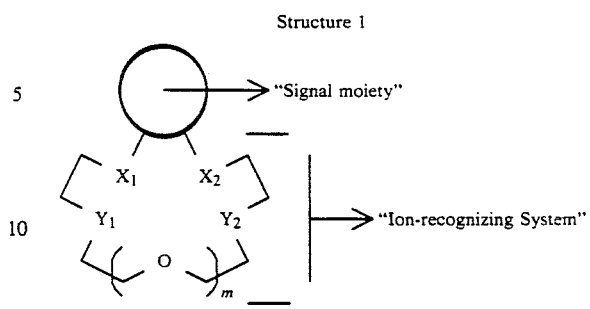

Structure 1 wherein said "signal moiety" is selected from the group consisting of fused ring heterocyclics and fused aromatics; and wherein said "ion recognizing system" is a crown ether wherein $X_1$ and $X_2$ of said crown ether are the same or different and are heteroatoms selected from the group consisting of oxygen (O), nitrogen (N), sulfur (S), phosphorous (P), and selenium (Se); and wherein $Y_1$ and $Y_2$ are the same or different and are carbon (C), nitrogen (N), oxygen (O), sulfur (S), selenium (Se) and phosphorus (P); and the repeating unit n is an integer from about 0–12.

In the preferred embodiments, the signal moiety is selected from the group consisting of coumarins and anthracenes; and said crown ether contains heteroatoms selected from the group consisting of O, N, S and P.

The preferred heteroatoms in the crown ether moiety as depicted in General Structure 1 are nitrogen (N) and oxygen (O); particularly O, and the repeating unit n is preferably an integer from about 0–3. Further, these ionophores function at neutral pH in aqueous or alcoholic media.

The present invention also provides a selective fluorogenic ionophore comprising a signal moiety bonded to a crown ether, said ionophore also having a "ligating arm" of the general formula:

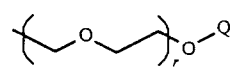

wherein r is about 0 to about 6 and Q is a quenching group. Representative structures are as follows:

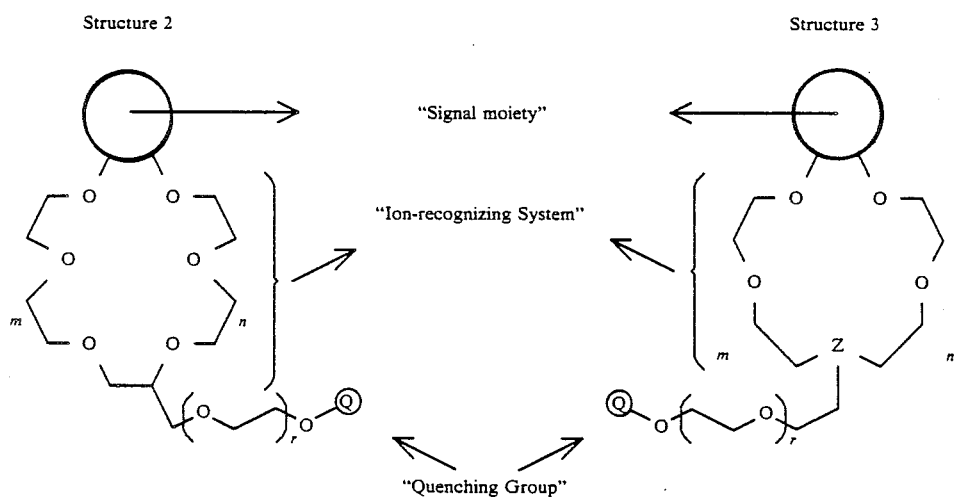

Structure 2

Structure 3 wherein the fluorescent moiety is as described above and the crown ether may incorporate one or more nitrogen atoms. The ligating arm is made of a polyethylene oxide chain bearing a quenching group Q at its terminal end, and n,m and r in structures 2 and 3 are integers which may be same or different and may range from 0-6.

BRIEF DESCRIPTION OF THE DRAWINGS

FIG. 8 compares the fluorescence emission spectra of 11-benzyloxymethyl-2,3-naphtho-18-crown-6(a) (without intra-molecular quenching) with that of 11-m-dinitrobenzoyloxymethyl-2,3-naphtho-18-crown-6(b) (with intra-molecular quenching).

DETAILED DESCRIPTION OF THE INVENTION

Figure 1:
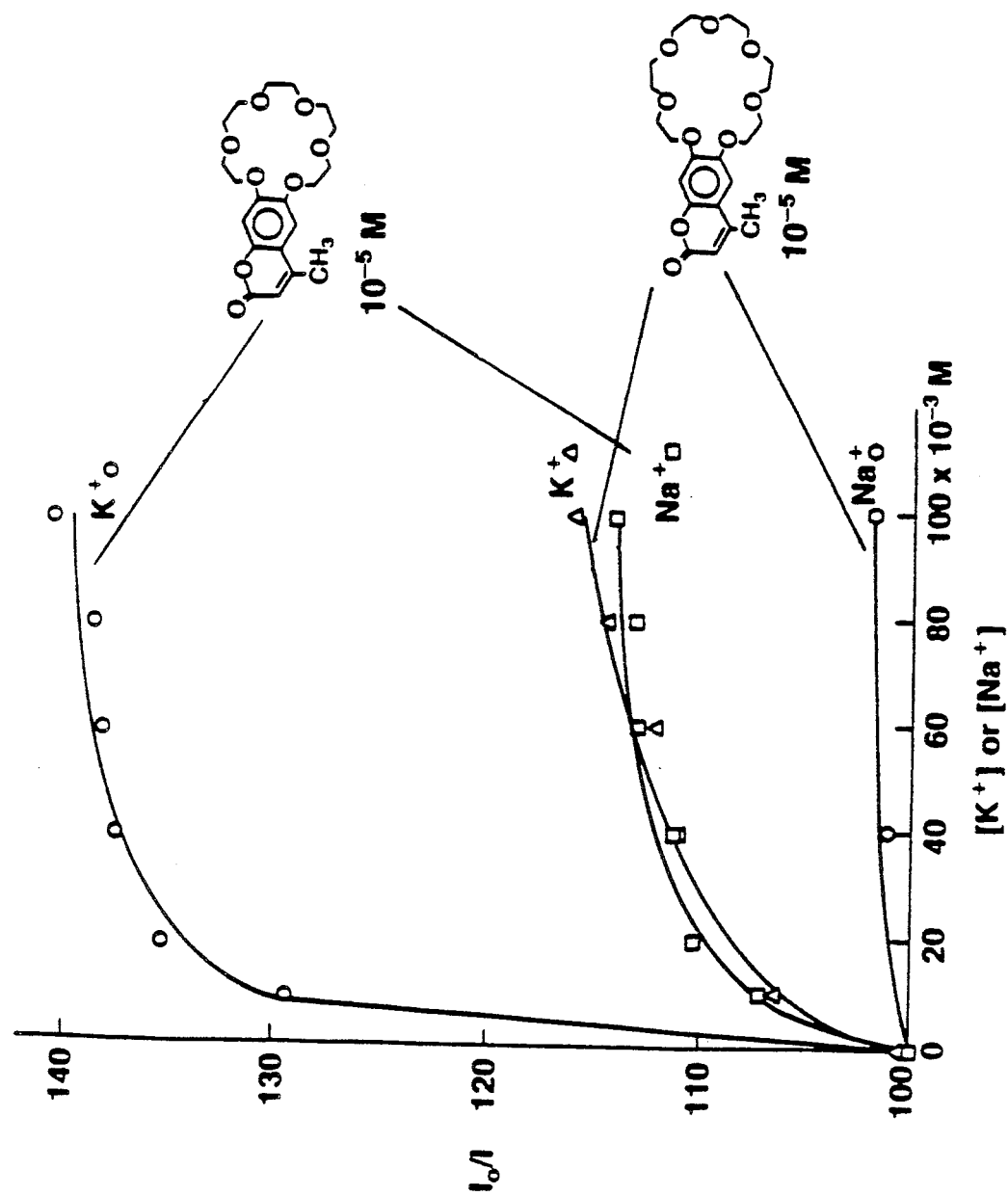
FIG. 1 depicts the graph of the ratio of fluorescence of ion-free ionophore to that ionophore bound to sodium or potassium ion (Io/I) versus concentration of sodium or potassium ion in 50/50 ethanol water for 6,7-(4-methyl) coumaro-18-crown-6 and 6,7-(4-methyl) coumaro-21-crown-7.

The selective reagent ionophores of the present invention comprise two moieties, a "signal moiety" and a crown ether moiety, the latter capable of complexing with various metal ions. In this sense, the crown ether forms the "ion-recognizing system." (See General Structure 1).

The "signal moiety" in the compounds of the invention is a chemical moiety bound to the "ion-recognizing" crown ether and can exhibit a change in optical properties upon complexing of a metal ion with said crown ether. This change in optical properties is evidenced fluorometrically when binding of the metal ion causes quenching or enhancement of fluorescence. Fluorescence measurements are preferred to absorption measurements since light intensities are measured against a dark background. Thus, the signal moiety in the fluorogenic crown ethers of the invention is designed to absorb light, preferably above 300 nm, and re-emit the absorbed light energy as fluorescence. The signal moiety contains a chromophoric group or several chromophoric groups, capable of efficient absorption of light energy. Of the preferred chromophores for fluorescent emission are those having carbonyl groups, carbon-carbon double bonds, and aromatic rings. In the preferred embodiments of the reagent ionophores of the invention, fused rings such as naphthalenes, anthracenes, benzofurans, benzodiazines, benztrioxazines, benzotriazepines, pyrenes, coumarins (or 1,2-benzopyrones) and the like are used as the fluorescent signal moiety. In the particularly preferred embodiments, a coumarin is the signal moiety, a typical structure being depected below.

Structure 4
Coumarin (1,2-Benzopyrone)

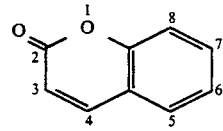

Of the preferred coumarins, are those having one or more substitutions at positions 3, 4, 5, 6 or 8. Illustrative substituents may be hydrogen, hydrocarbons, esters, acids, fluorinated hydrocarbons, aromatic groups, ethers, thiols, thioethers or various combinations of these groups, and the like. Structure 5 (a) and (b) is representative (substituents indicated by $R_1-R_4$):

Structure 5

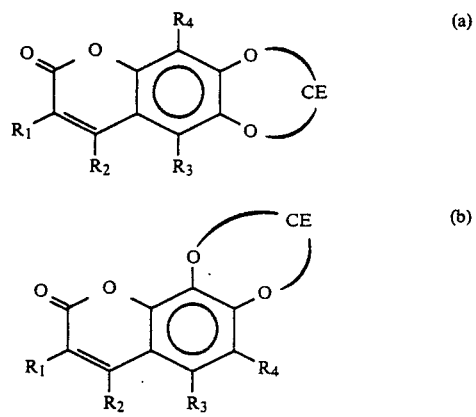

wherein $R_1$, $R_2$, $R_3$, $R_4$ are the same or different and are H, hydroxy, amine, alkyl, aryl, fluorocarbon, ester, acid, ether, thiol, or thioether (and CE=crown ether).

In the more preferred embodiments, substituting the hydrogen at position 7 in the coumarin ring with a heteroatom with lone pairs of electrons has been discovered to enhance the quantum yield of fluorescence. While the present inventors do not wish to be bound by theory, this may be due to the stabilization of the dipolar form, as illustrated by the following Structures, containing oxygen atom which increases the transition moment of the lowest energy electronic excitation of the molecule:

Structure 6

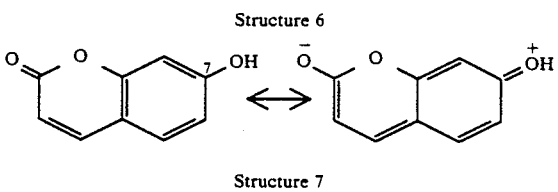

Structure 7

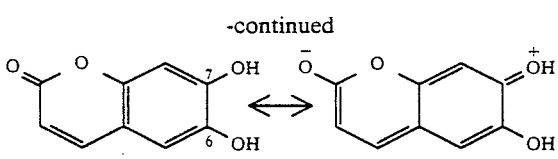

A particularly preferred reagent ionophore of the invention comprises 4-methylcoumarin fused to a crown ether through positions 6 and 7 or 7 and 8. The fusion may be through two heteroatoms such as P, S, N, O or Se, which may be the same or different at these positions. However, it is particularly preferred that O be the heteroatom at both of the positions. The following structures depict certain preferred embodiments.

Structure 8

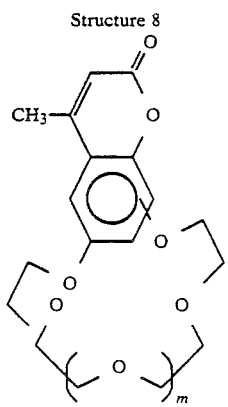

Structure 9

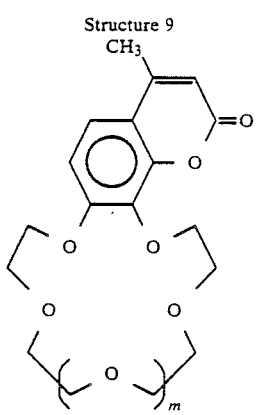

Although the present inventors do not wish to be bound by scientific theory, or in any other way be limited thereby, they have discovered that when irradiated, compounds such as those shown in the above illustrations may be excited to polar states. It has been postulated that when the metal ion binds to the ionophore, it drains the electrons from the heteroatoms of the ionophore and thus causes electronic perturbations in these heteroatoms, i.e.: the electrons flow from the heteroatoms to the newly complexed metal ion. In the compounds of the present invention, one of the heteroatoms is a source of electrons transferred to the remote carbonyl oxygen in the process of optical excitation. The molecule as a whole responds to the presence of a selectively bound metal ion causing a change in fluorescence emission. This change is used to deduce the presence of and, if desired, to quantitate the amount of the target metal ion that has been drawn from its surrounding medium to bind to the ionophore. Thus, the signal moiety serves as an optical transducer for measuring the ion-recognizing capability of the ionophore.

The ion recognizing moiety of the novel compounds of the invention is a crown ether that can vary widely with respect to its ring diameter. In general, the ring diameter should approximately match the ionic diameter of the ion it is desired to accommodate. It is thus preferred that the ring diameter not be substantially larger or smaller than the ionic diameter. In this sense, it is preferred that the ring diameter not vary from the ionic diameter of the ion by more than about ±0.8 Å, preferably not more than about ±0.5 Å, and most preferably not more than about ±0.2 Å.

It should be appreciated that the crown ethers are selected according to their cavity diameters for detection of particular ions. For example, lithium ion has an ionic diameter of 1.2 Å, sodium ion, approximately 1.9 Å and potassium ion approximately 2.66 Å. The cavity diameter can thus be varied from about 1.3 Å to about 3.0 Å in order to selectively accommodate these particular ions. One skilled in the art will understand that the cavity size can be progressively increased by increasing the number of bridging ethoxy groups (for example increase the number of the repeating unit from 0 to 12 in structures 8 and 9).

More specifically, 18-crown-6 (Structure 10), 21-crown-7 (Structure 11) and their monoaza and diaza analogs with a cavity diameter of 2.6–3.2 Å and 3.4–4.3 Å respectively, are selective in binding potassium ion. 15-crown-5 (Structure 12) and its monoaza analogs, with a cavity diameter of 1.7–2.2 Å binds sodium ion selectively. These three crown ether systems are preferred as the ion-recognizing moieties of the reagents of the invention.

Structure 10

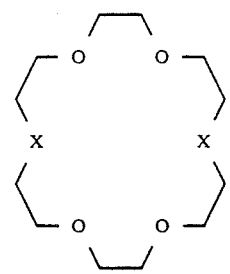

Structure 11

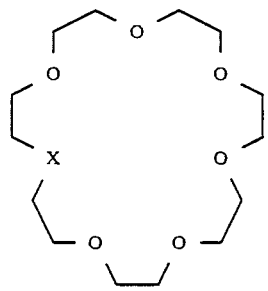

Sturcture 12

Structure 13

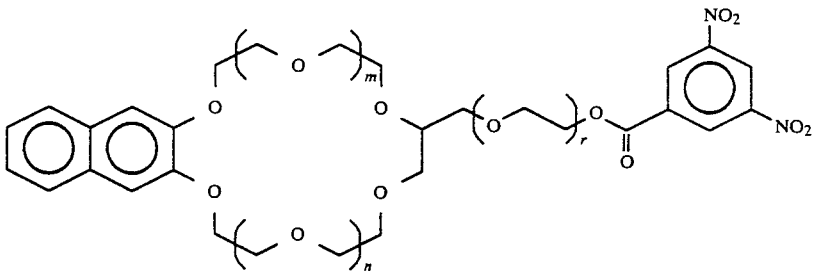

Structure 14

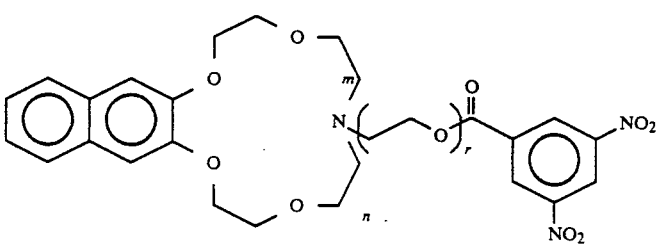

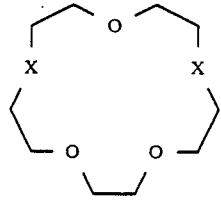

X = O or NH

In some embodiments of the present invention, a "ligating arm" bearing a fluorescence quenching group at its terminal end is bound to the crown ether. As used herein, "ligating arm" (also known as "lariat") is a linear chain made of ethylene oxide units attached to the crown ether, but is not part of the ring. The length of the arm may vary widely in the number of ethylene oxide units. A preferred number of units is about 0–10, with about 0–5 particularly preferred.

While not wishing to be bound by theory, the present inventors believe that the ether oxygens of this linear chain provide an additional ligating center which may be folded over and bound to the metal ion sequestered in the crown ether part, thus providing an additional mechanism for electronic modulation of the fluorescence properties of the system. In other words, this system resembles cryptands in their ability to bind metal ions. Bicyclic cryptands are known to be more selective and sensitive as ionophores to metal ion binding than crown ethers. (J. M. Lehn "Cryptates: Macrocyclic Inclusion Complexes," Pure & Appl. Chem. 1977, 49, 857–870.)

The ligating arm in the ionophores of the invention also has a terminal quenching group "Q". This quenching group may serve to enhance the fluorescence emission or quench fluorescence when the ionophore is bound to the metal ion for which it is selective. Illustrative of suitable quenching groups are esters or corresponding ketones such as chloracetate, bromoacetate, m-dinitrobenzoate, methylketone, phenones, carbonyl containing groups such as benzoyl, cyclohexyl carbonyl, and carboxyl-containing groups such as acetates, propionates, and the like. Illustrative of representative crown ethers bearing ligating arms are:

where m,n and r are integers which may be the same or different and range from about 0–5. The m-dinitrobenzoate group at the terminal end of the ligating arm is believed to facilitate the intra-molecular quenching of the naphthalene fluorescence.

The positioning of the quenching group relative to the naphthalene ring depends on the dimension of the crown ether, the size of the metal ion complexed, and the number of ethylene oxide units in the ligating arm. Although the present inventors do not wish to be bound by theory, they believe that the quenching efficiency may be sensitive to the distance between the fluorescing group and the quenching group, and decreases as the sixth power of this distance. Thus, one may observe selective fluorescence quenching or enhanced fluorescence emission with the metal ion for which the ionophore is designed. Such changes in fluorescence intensity is a measure of the concentration of this particular metal ion in a given sample even though other ions may be present.

In Structures such as 13 and 14, fluorogenic groups other than naphthalene may be substituted. Example of such groups are anthracenes, phenanthrenes, pyrenes, coumarins and the like. Preferred quenching groups Q are chloroacetate and bromoacetyl, and carbonyl groups such as benzoyl, cyclohexyl, carboxyl groups, methyl ketones, phenones and the like.

The reagent ionophores of the invention may be prepared by conventional processes available in the open literature for incorporation of symmetrical bifunctional compounds into closed ring products. However, the synthesis of the preferred coumaro-crown ethers of the invention may be achieved by a cyclization procedure which incorporates unsymmetric bifunctional compounds into closed ring products. By way of illustration, commercially available 4-methylesculetin (6,7-dihydroxy-4-methylcoumarin) may be reacted with one mole equivalent of an appropriate $\alpha,\omega$-diiodo polyethylene oxide. The reaction of 4-methylesculetin with one mole equivalent of 1,14-diiodo-3,6,9,12-tetraoxatetradecane in refluxing acetonitrile (0.03M) in the presence of seven molar equivalent of anhydrous potassium fluoride can produce the 6,7-(4-methyl) coumaro-18-crown-6 (6',7'-(4'-methyl)coumaro-1,4,7,10,13,16-hexaoxacyclooctadeca-2-ene) in five days in 85% yield. The compound may be purified by HPLC and confirmed by conventional techniques as infrared. ¹H NMR and fast atom bombardment mass spectrometry (FABMS). The preferred structure, 6,7-(4-methyl) coumaro-18-crown-6, is shown below Structure 15

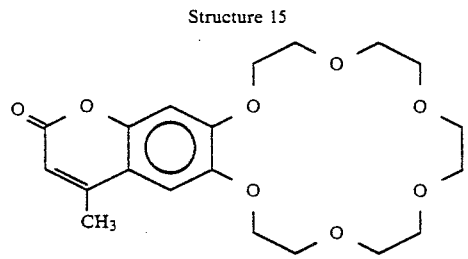

In a similar manner, 6,7-(4-methyl) coumaro-21-crown-7 [6',7'-(4'-methyl) coumaro-1,4,7,10,13,16,19-heptaoxa-cyclohenicosa-2-ene], another preferred ionophore, may be prepared from 4-methylesculetin and 1,17-diiodo-3,6,9,12,15-pentaoxaheptadecane in yields as high as 40%. The structure of this ionophore is shown below:

Structure 16

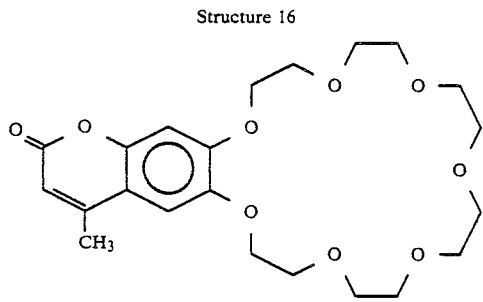

6,7-(4-methyl) coumaro-15-crown-5 [6',7'-(4'-methyl) coumaro-1,4,7,10,13-pentaoxacyclopentadeca-2-ene] may be prepared from 4-methylesculetin and 1,13-diiodo-3,6,9-trioxaundecane in yields as high as 85%. The structure of this compound is shown below.

Structure 17

-continued

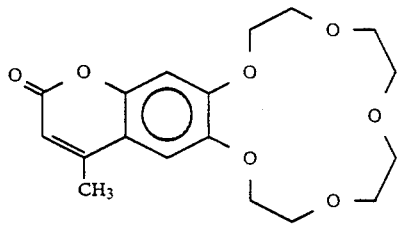

In other preferred embodiments, naphtho-crown ethers having ligating side arms may be prepared from 2,3-dihydroxynaphthalene. The disodium salt of this compound may be reacted with two mole equivalents of 2-(2-chloroethoxy)-ethanol in DMF at 80° to form a dihydroxy compound which may then be converted to the corresponding dichloro compound using thionyl chloride in the presence of pyridine in refluxing toluene. The dichloro compound may then be reacted with the dilithio alkoxy derivative of 3-O-benzyloxy-sn-glycerol in refluxing t-butanol in the presence of lithium bromide to form 11-benzyloxymethyl-2,3-naphtho-18-crown-6. Hydrogenolysis Pd/carbon/ethanol) of this compound followed by reaction with m-dinitrobenzoyl chloride in the presence of pyridine produces the 11-(m-dinitrobenzoyloxymethyl)-2,3-naphtho-18-crown-6. The structure of this compound is shown below:

Structure 18

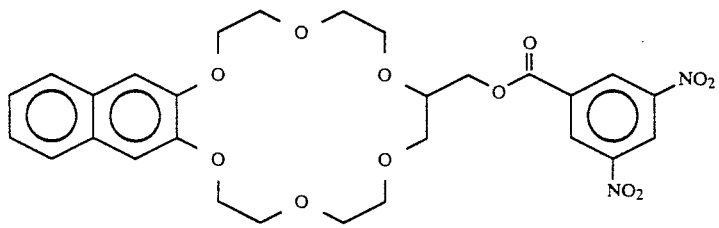

In another preferred embodiment of this invention, the dichloro compound described in the preceeding paragraph may be reacted with benzylamine to form N-benzyl-2,3-naphtho-10-aza-15-crown-5 shown in Structure 19 below:

Structure 19

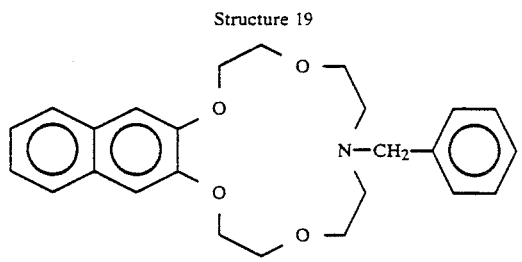

The benzyl group from this compound is removed by hydrogenolysis and the aza crown ether is then attached to an appropriate ligating side arm with a m-dinitrobenzyloxy terminal group.

In its broadest aspect, the method of using the compounds of the invention as reagent ionophores to detect ions may be carried out by simply contacting the ionophore with the sample which may contain the target ions. Detection of ions using the ionophores of the invention may take place in liquid media varying widely in composition. For example, a purely alcoholic medium, a purely aqueous medium, or a mixture of both is suitable. However, if the reagent ionophore is used in a liquid form, it is preferably in a solution medium that is compatible with the sample under analysis.

It should be appreciated that the present reagent ionophores do function quite well in neutral or basic pH media. Thus, monitoring of crude biological systems is possible with these reagents. Crude biological, physiological, environmental samples and the like may be assayed in their natural states for ion content, preferably after minimum sample preparation is performed, such as freeing the sample of suspended impurities and the like. The latter may be accomplished by filtration, sedimentation, centrifigation, or any other suitable conventional technique. However, it should be appreciated that the pH of the medium should preferably be above 6.0. Thus, if it is desired to analyze a highly acidic sample, such as for example, stomach contents or the like, the sample should be neutralized prior to analysis. The pH of the medium assayed preferably ranges between about 7 to about 12.

The compounds of the invention may be used as reagent ionophores in solution for use in the detection of ions. Concentrations of reagent ionophores may vary widely according to the ionophore utilized and the medium in which ion detection is to take place. Hence, any concentration that serves to complex with an ion in a given medium may be utilized, and one skilled in the art will readily appreciate that concentrations of ionophore may be optimized. However, the present inventors have discovered that when reagent ionophores are used in a water/ethanol solution system, a preferred concentration of reagent ionophore is about $2.10^{-5}M$ to about $1.10^{-4}M$. These preferred ranges help to avoid self-quenching by the ionophores.

The compounds may also be immobilized by conventional techniques for use as a reagent ionophore, such as by dispersing the compound in a matrix, such as a polymer matrix. Other possibilities include chemical attachment of the compound to matrix components or conventional solid supports. When so immobilized, the concentration of ionophore may then vary widely and can be increased beyond $1.10^{-4}M$. Self-quenching is not a factor in this situation.

The detectability range of the reagent ionophores of the present invention for ions varies widely according to the ion it is desired to detect and the medium in which detection takes place. The maximum fluorescence efficiency for fluorogenic ionophores described above is expected to be observed at about $10^{-4}M$ concentration. Above this concentration, the fluorescence emission may be expected to decrease due to self-quenching. One skilled in the art will appreciate that the range of concentrations of the analyte ion within which it can be determined quantitatively with good precision by concentration of the analyte ion over which it may be detected by range of a given fluorogenic ionophore may be established by dissolving known amounts of the ion in approximately a $10^{-5}M$ solution of the ionophore, and plotting ratios of fluorescence emission values (Io/I) against ion concentrations. Plots such as these are conventionally used as standards against which emission values from a sample containing an unknown concentration of ion may be compared, to thus determine the unknown concentration of ion in the sample.

With respect to the detection of potassium ion, a plot of the ratio of fluorescence (Io/I) of a $10^{-5}M$ 6,7-(4-methyl)coumaro-18-crown-6 and 6,7-(4-methyl)-coumaro-21-crown-7 against ion concentration (FIG. 1) shows a limiting value at $60 \times 10^{-3}M$ for the 18-crown-6 and $100 \times 10^{-3}M$ for the 21-crown-7 systems. However, sodium ion also shows significant quenching for the 6,7-(4-methyl)coumaro-18-crown-6 while its effect on the 6,7-(4-methyl)coumaro-21-crown-7 is small. Thus, it would appear that 6,7-(4-methyl)coumaro-21-crown-7 is more selective for potassium ion than the corresponding 18-crown-6 system. This appears to be so in spite of the latter system giving greater response to changes in the potassium ion concentrations. The former is therefore more selective even though it is less sensitive of the two ionophores. (See also FIGS. 3 and 5.)

The ranges of detection capability may however be increased by a variety of means. For example, one skilled in the art will appreciate that a sample containing a high concentration of the ion under investigation may be diluted so that the concentration of the ion will fall within the optimum range of its detectability. A second approach may be to immobilize the ionophore to a solid surface by conventional techniques. Immobilization will prevent self-quenching and the detectability range can be extended by increasing the loading levels of the immobilized ionophore, so that there is more reagent ionophore available for complexing. In addition, selective sequestering of interfering ions may be accomplished by adding a known excess of a non-photoresponsive ionophore, or attaching such a nonphotoactive ionophore to a polymer backbone to remove the interfering ion from the solution. (J. Nuclear Sci. & Technol., 1983, 20, 439-440).

The ionophores of the present invention may be used in many diverse applications wherein it is desired to detect specific ions. Ionophores selective for potassium ion are of interest in the fast and accurate determination of these ions in body fluids and the like. Fluorogenic ionophores selective for potassium can be used in reagent kits, and conventional protocols may be easily developed for mixing a solution, preferably an alcoholic solution of the ionophore with blood serum samples, and then measuring potassium using fluorescence spectrophotometers. The present inventors have discovered that representative ionophores of the present invention are stable for a long period of time in aqueous and alcoholic solutions, and thus, these are the preferred solution media.

The fluorogenic ionophores can also be incorporated in fiber optic-based automated analytical instruments, especially bifurcated fiber optics. For example the fluorogenic ionophore may be immobilized at the terminal ends of conventional optic fibers, or a solution of the ionophore may be contacted with an optic fiber using a sensor cap provided with a permeable membrane for the transport of ions into the sensor cap. One branch of the bifurcated fiber optic may thus carry the light for excitation, while the other branch may carry the fluorescence emission. Optical sensors using fiber optics have a number of advantages over electrochemical sensors. First, they do not require reference signals, and second, because the primary signal is optical, it is not subject to electrical disturbances such as those arising from surface potentials. Optical sensors can measure concentrations of the target ions without significantly disturbing the sample, and can thus be used for continuous monitoring, an example of which is the in vivo monitoring of potassium ion in the human blood during surgery. Fiber optic-based sensors also offer the advantage that the signal can be transmitted over long distances (about 2-100 meters) thus facilitating remote sensing. Further, they are amenable to miniaturization.

Certain ionophores of this invention preferentially complex with sodium ion, resulting in fluorescence quenching. These can be used to develop test kits or fiber optic-based sensors for detecting sodium ion. One example of this is in the detection of leakage of sea water into electronic instruments in towed arrays for sonar sensing or in reusable booster rockets used in launching vehicles into outer space.

Binding of the target ions by the ionophores will modulate their electrical as well as their optical properties. Chemical analogues of certain of the preferred fluorogenic reagents may therefore be used for developing electrical sensors such as ion-selective Field Effect Transistors (FETs). In one such embodiment. FETs are electronic switching devices which can be used in turning on an alarm when sea water leaks occur. The ionophore is covalently bound to the surface oxygens of an inorganic insulator such as silica, alumina, thoria and the like. Since the fluorogenic ionophores of the invention are especially efficient in transmitting electronic perturbations, one may expect that modulation of the electric potentials "seen" by the FETs will occur when targeted ions are bound to the ionophores. An example of this is a sea water leakage warning system. When contacted with sea water, the sodium ion complexes with the ionophore-based FET, thus affecting the output voltage of the FET amplifier. Such voltage changes can set off an alarm.

The following are more specific embodiments of the present invention, and are not to be considered limitative thereof.

EXAMPLE 1

Preparation of
1,14-Dichloro-3,6,9,12-tetraoxatetradecane

A solution of 2.4 g of pentaethyleneglycol and 2.4 g of pyridine in 20 ml of anhydrous toluene are stirred and heated to 70° under a nitrogen atmosphere. 2.4 g of thionyl chloride are added over a period of 15 minutes under vigorous agitation. The mixture is heated at reflux temperature for 21 hours. After cooling to ambient temperature the solution is decanted. The residue is broken up, washed with toluene and combined with the supernatent liquid. This solution is washed with dilute hydrochloric acid, then saturated NaCl solution. The organic layer is separated, dried ($Na_2SO_4$ and evaporated to form the title compound. Yield 69%.

EXAMPLE 2

Preparation of
1,14-Diiodo-3,6,9,12-tetraoxa-tetradecane

A solution of 2.8 g of the dichloride obtained in Example 1 and 3.8 g of anhydrous sodium iodide in 35 ml of anhydrous acetone and heated at reflux temperature for 20 hours. After cooling to ambient temperature the solution is evaporated to dryness. The solid residue is dissolved in chloroform and washed with a sodium thiosulfate solution to remove iodine. The organic layer is separated, dried ($Na_2SO_4$), and evaporated to form the diiodo compound. Yield 83%.

EXAMPLE 3

Preparation of 6,7-(4-methyl)-coumaro-18-crown-6.

A solution of 4.6 g of the diiodide obtained in Example 2 and 1.9 g of 6,7-dihydroxy-4-methylcoumarin in 350 ml of anhydrous acetonitrile are stirred with 4.0 g of anhydrous potassium fluoride under a nitrogen atmosphere and heated at reflux temperature for 5 days. After cooling to ambient temperature the solution is evaporated to dryness. The solid residue is dissolved in chloroform and washed with 2% sodium hydroxide solution. The organic layer is separated, dried over sodium sulfate and evaporated to dryness to give the crude product (85% yield). Purification by HPLC on a C-18 column with mobile phase of 80% acetonitrile/20% water at 2 ml/min (UV detector 260 nm) gives the crystalline title compound. Yield 36%: IR 1715 $cm^{-1}$ ($\alpha,\beta$-unsaturated $\delta$-lactone C=O); $^1$H NMR ($CDCl_3$) $\delta$ 7.0 (s,1H), 6.82(s,1H), 6.15(s,1H), 4.2 (t,4H), 3.95(m,4H), 3.77(m,4H), 3.71(m,4H), 3.68(m,4H), 2.39(s,3H); MS(FAB) 395 (M+H), 417(M+Na), 433(M+K); UV(50% $CH_3CH_2OH$) $\lambda$ max($\epsilon$) 229 (20,400), 290(5,890), 340(12,260); fluorescence (50% $CH_3CH_2OH$) $\lambda$ ex 330 nm, 80 em 340-540 nm (broad) with maximum at 410 nm.

EXAMPLE 4

Preparation of
1,17-Dichloro-3,6,9,12,15-pentaoxaheptadecane

In a manner similar to that described in Example 1 a solution of 2.8 g of hexaethylene glycol and 2.4 g of pyridine in 20 ml of anhydrous toluene are stirred and heated to 70° under a nitrogen atmosphere. 2.4 g of thionyl chloride are added over a period of 10 minutes under vigorous agitation. The mixture is heated at reflux temperature for 20 hours. Continue as Example 1. The title compound was obtained in 68% yield.

EXAMPLE 5

Preparation of
1,17-Diiodo-3,6,9,12,15-pentaoxaheptadecane

In a manner similar to that described in Example 2, a solution of 3.2 g of the dichloride obtained in Example 4 and 3.8 g of anhydrous sodium iodide in 35 ml of anhydrous acetone are stirred under a nitrogen atmosphere and heated at reflux temperature for 20 hours. Continue as Example 2. The anticipated diiodo compound was obtained in 81% yield.

EXAMPLE 6

Preparation of 6,7-(4-methyl)-Coumaro-21-crown-7.

In a manner similar to that described in Example 3, a solution of 5.0 g of the diiodide obtained in Example 5 and 1.9 g of 6.7-dihydroxy-4-methylcoumarin in 350 ml of anhydrous acetonitrile are stirred with 4.0 g of anhydrous potassium fluoride under a nitrogen atmosphere and heated to reflux temperature for 6 days. After cooling to ambient temperature the solution is evaporated to dryness. The solid residue is dissolved in chloroform and washed with 2% sodium hydroxide solution. The organic layer is separated, dried ($Na_2SO_4$) and evaporated. Purification on alumina with mobile phase of ethylacetate and 1% methanol provided the colorless crystalline title compound in 41% yield. IR 1718 $cm^{-1}$ ($\alpha,\beta$-unsaturated $\delta$-lactone C=O); $^1$H NMR $\delta$ 6.97 (s,1H), 6.75 (s,1H), 6.09 (s,1H), 4.14 (m,4H), 3.88

(m,4H), 3.73 (m,4H), 3.67 (m,4H), 3.60 (br s, 8H), 2.30 (s, 3H); MS(FAB) 461 (M+Na), 477 (M+K); Anal. Calcd for $C_{22}H_{30}O_9$: C, 60.27; H, 6.90. Found: C, 60.66; H, 6.87; UV (50% $CH_3CH_2OH$) λmax (ε)228 (20,160), 290 (6,070), 340 (13,140); fluorescence (50% $CH_3CH_2OH$) λex 330 nm, λem 340–540 nm (broad) with peak at 410 nm.

EXAMPLE 7

Preparation of 1,13-Dichloro-3,6,9-trioxaundecane

In a manner similar to that described in Example 1, a solution of 1.9 g of tetraethylene glycol and 2.4 g of pyridine in 20 ml of anhydrous toluene and stirred and heated to 70° under a nitrogen atmosphere. 2.4 g of thionyl chloride are added, over a period of 10 minutes under vigorous agitation. The mixture is heated at reflux temperature for 20 hours. Continue as Example 1. The title compound was obtained in 70% yield.

EXAMPLE 8

Preparation of 1,13-Diiodo-3,6,9-trioxaundecane

In a manner similar to that described in Example 2, 2.3 g of the dichloride obtained in Example 7 and 3.8 g of anhydrous sodium iodide in 50 ml of anhydrous acetone are stirred under a nitrogen atmosphere and heated at reflux temperature for 70 hours. Continue as Example 2. The diiodo compound was obtained in 96% yield.

EXAMPLE 9

Preparation of 6,7-(4-methyl)-coumaro-15-crown-5

In a manner similar to that described in Example 3, a solution of 4.1 g of the diiodide obtained in Example 8 and 1.9 g of 6,7-dihydroxy-4-methylcoumarin in 350 ml of anhydrous acetonitrile are stirred with 4.0 g of anhydrous potassium fluoride under a nitrogen atmosphere and heated to reflux temperature for 9 days. After cooling to ambient temperature the solution is evaporated to dryness. The solid residue is dissolved in chloroform and washed with 2% sodium hydroxide solution. The organic layer is separated, dried ($Na_2SO_4$) and evaporated. Yield 85%. Purification on alumina with mobile phase of ethyl acetate and 1% methanol gives the crystalline title compound. Yield 23%: IR 1718 cm$^{-1}$ (α,β-unsaturated δ-lactone C=O); $^1$H NMR δ 7.0 (s,1H). 6.8 (s,1H), 6.15 (s,1H), 4.2 (t,4H), 3.95 (m, 4H), 3.8 (m,4H), 3.7 (m,4H), 2.4 (s,3H); MS(FAB) 351 (M+H), 373 (M+Na); UV (50% $CH_3CH_2OH$)λmax (ε) 226 (18,370), 287(5,500), 339(12,110); fluorescence (50% $CH_3CH_2OH$) λex 330 nm, λem 340–540 nm (peak at 410 nm).

EXAMPLE 10

Preparation of 2,3-naphtho-bis (6-hydroxy-1,4-dioxa) hexane

Sixteen grams of 2,3-dihydroxynaphthalene dissolved in 50 mL of N,N-dimethylformamide (DMF) with 0.01 g of dibenzo-18-crown-6 was added to a stirring solution of 8 g of powdered sodium hydroxide in 35 mL of DMF under nitrogen at 80°. When the mixture clears up, 25 g of 2-(2-chloroethoxy) ethanol dissolved in 50 mL of DMF are added over a period of 30 minutes and the mixture heated to 90° for 18 hours. After cooling to ambient temperature, chloroform is added and washed with 2% sodium hydroxide solution. The organic layer is separated, dried ($Na_2SO_4$) and evaporated to dryness to give the title compound in 33% yield. $^1$H NMR (CDCl$_3$) δ 7.1–7.8 (m,6H), 4.1–4.4 (m,4H), 3.8–4.1 (m,4H), 3.7 (br s, 10H).

EXAMPLE 11

Preparation of 2,3-naphtho-bis(6-chloro-1,4-dioxa)hexane

In a manner similar to that described in Example 1, a solution of 3.3 g of the diol obtained in Example 10 and 0.8 g of pyridine in 75 mL of anhydrous toluene are stirred and heated at 70° under nitrogen. Thionyl chloride (3.1 g) was added over a period of 10 minutes under agitation. The mixture is heated under reflux for 18 hours. After work up (same as described in Example 1) the title compound was obtained in 82% yield.

EXAMPLE 12

Preparation of 11-Benzyloxymethyl-2,3-naphtho-18-crown-6

Lithium (0.31 mole, 2.15 g) from a 30% lithium in oil suspension was placed in a 1L three-neck flask under nitrogen. t-Butanol (500 mL) was added slowly at first. Lithium t-butoxide was rapidly formed and hydrogen gas was liberated. After refluxing for an hour, 0.1 mole (18.22 g) of 3-O-benzyl-sn-glycerol (prepared according to the procedure of B. T. Golding and P. V. Ioannon, Synthesis, 1977, 423–424) was added to form the dilithium salt of this diol. After refluxing for another half hour, the dichloro compound from Example 11 (25.63 g, 0.07 mole) was added followed by 0.1 mol of LiBr.-$H_2O$. The mixture was refluxed for two weeks. t-Butanol was removed and the residue treated with water and neutralized with hydrochloric acid. The aqueous medium was extracted four times with 75 mL of $CH_2Cl_2$ and the combined organic layer was dried ($Na_2SO_4$) and concentrated to yield 59.3 g of crude brownish solid. Purification by column chromatography on neutral alumina using ethylacetate/ether/methanol provided the pure title compound. The $^1$H NMR and IR spectroscopy were found to be identical to those reported by B. P. Czech etal, Synthesis, 1985, 314–316.

EXAMPLE 13

Preparation of 11-(m-dinitrobenzoyloxymethyl)-2,3-naphtho-18-crown-6

Hydrogenolysis of the benzyl group from the compound prepared as described in Example 12, was achieved by dissolving 1 g of the compound in formic acid (2 g) with 0.15 g of 10% palladium on carbon and stirring the mixture under hydrogen (60 psig) at 110°. The product was cooled and poured into 100 mL of $CH_2Cl_2$. After filtering off the catalyst, the organic solvent was extracted with sodium bicarbonate solution (to remove formic acid), dried ($Na_2SO_4$) and concentrated. The formate ester of 11-hydroxymethyl-2,3-naphtho-18-crown-6 was obtained in quantitative yield. [IR 1720 cm$^{-1}$ (ester carbonyl); $^1$H NMR (CDCl$_3$) δ 8.0 (s 1H), 7.1–7.8 (m, 6H). 4.1–4.5 (m, 6H), 3.6–4.1 (m, 15H)]. The formate ester was suspended in water (30 mL) and heated at 100° for two days in the presence of hydrochloric acid (10% in water). The product was extracted with $CH_2Cl_2$ and washed with saturated sodium bicarbonate solution. The organic layer was then dried ($Na_2SO_4$) and concentrated to yield 80% of the 11-hydroxymethyl-2,3-naphtho-18-crown-6. [IR 3380 cm$^{-1}$ (—OH); $^1$H NMR (CDCl$_3$) δ 7.18–7.9 (m, 6H), 4.2–4.5 (m, 4H), 3.15–4.2 (m, 18H); MS(FAB) 415 (M+Na), 431 (M+K) indicating molecular weight of 392.] One millimole of this compound was added to a stirring solution of one millimole of m-dinitrobenzoyl chloride and 1–2 millimole of pyridine in 10 mL of dry toluene at 55°. The mixture was heated at 55° for three hours. After cooling, toluene was transferred to a separatory funnel. The residue was washed with 20 mL of toluene and the wash added to the separatory funnel. The toluene solution was washed with 15 mL of dilute HCl and later with saturated sodium chloride solution. The toluene layer was dried ($Na_2SO_4$) and concentrated to form 11-(m-dinitrobenzoyloxymethyl) 2,3-naphtho-18-crown-6 in 85% yeild. The product was purified over an alumina column using ethylacetate as eluent. Yellow crystals were obtained which showed only one yellow spot in TLC. $^1H$ NMR (CDCl$_3$) δ 8.8 (br s, 3H), 6.9–7.65 (m, 6H), 3.6–4.8 (m, 21H); MS(FAB) 625 (M+K), 609 (M+Na) 604 (M+NH$_4$) confirming the anticipated molecular weight of 586.

EXAMPLE 14

Preparation of N-benzyl-2,3-naphto-10-aza-15-crown-5

The diol obtained by the procedure described in Example 10 was converted to its dimesylate ester by the following procedure. The diol (1.88 g) and triethylamine (2.93 g) were stirred in 40 mL of $CH_2Cl_2$ at −10°. Methylsulfonyl chloride (3.5 g) in 40 mL of $CH_2Cl_2$ was added over a period of 20 minutes. After stirring for another 20 minutes, the product was diluted with 60 mL of cold $CH_2Cl_2$. Water (20 mL) was added, the organic layer separated then washed with saturated bicarbonate solution (2×15 mL) and dried ($Na_2SO_4$) and concentrated. The product (2.72 g, 98% yield) was confirmed by $^1H$ NMR to be the desired dimesylate. $^1H$ NMR (CDCl$_3$) δ 7.7 (m, 2H), 7.4 (m, 2H), 7.2 (s, 2H), 4.5 (t,4H), 4.3 (t,4H), 4.15 (t, 4H), 3.95 (t, 4H), 3.1 (s, 6).

The dimesylate (2.71 g) was dissolved in 80 mL of acetonitrile. To this solution was added 2.8 g of sodium carbonate and 0.64 g of benzylamine. The mixture was refluxed for 48 hours. The product was filter and the filtrate was concentrated. The residue was then dissolved in 80 mL of $CH_2Cl_2$ and washed with 3×50 mL of water and dried over anhydrous sodium sulfate. After filtering off the sodium sulfate, the filtrate was concentrated to obtain the N-benzyl-2,3-naphtha-10-aza-15-crown-5 in 65% yield. $^1H$ NMR (DMSO-d$_6$) δ 7.7 (m, 2H), 7.28 (m, 9H), 4.16 (br.s, 4H), 3.8 (m, 4H), 3.7 (br. 6H), 2.7 (br.s, 4H); MS (FAB) 408 (M+H), 330 (MH-C$_6$H$_6$), 316 (MH-C$_7$H$_8$).

EXAMPLE 15

Figure 2:
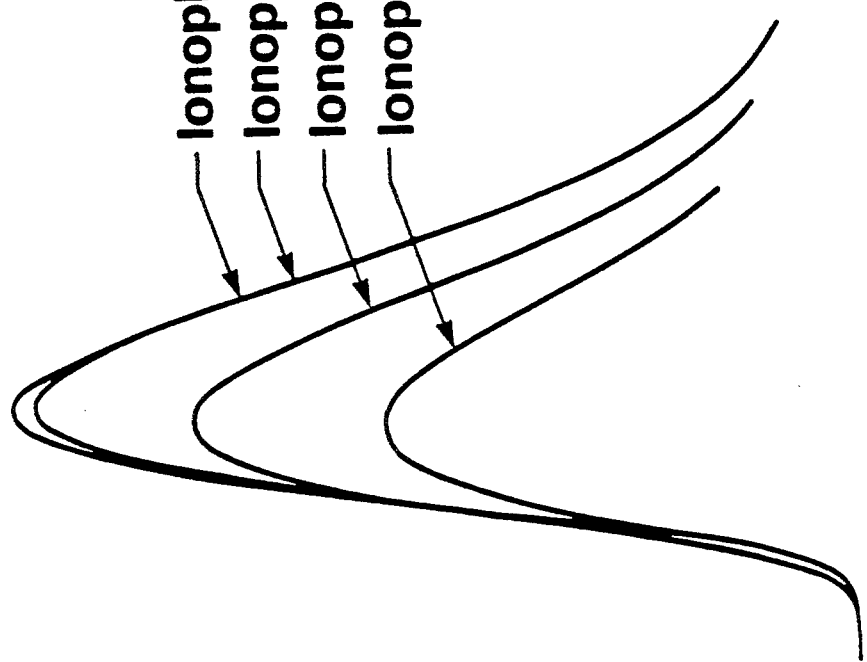
FIG. 2 depicts selective quenching of fluorescence of 6,7-(4-methyl) coumaro-18-crown-6 upon binding with potassium ion.

Selectivity of 6,7-(4-methyl)coumaro-18-crown-6 for potassium ion 6,7-(4-methyl)coumaro-18-crown-6 was taken at $10^{-5}M$ in ethanol at neutral pH. Fluorescence measurements were made at ambient temperature using exciting wavelength of 330 nm and scanning emission wavelengths from 340–540 nm giving a broad peak with maximum at 410 nm. The addition of one drop of 1M potassium chloride solution to 2.5 mL of the ionophore solution in a cuvette resulted in a dramatic quenching of the fluorescence emission. On the other hand, addition of one drop of 1M sodium chloride solution resulted in a slight quenching of the fluorescence. Addition of lithium chloride showed very little change (see FIG. 2).

This experiment demonstrates that the above inophore is a selective indicator for potassium ion.

EXAMPLE 16

Quantitative analysis of potassium ion in serum-like solutions using 6,7-(4-methyl)coumaro-18-crown-6

Figure 3:
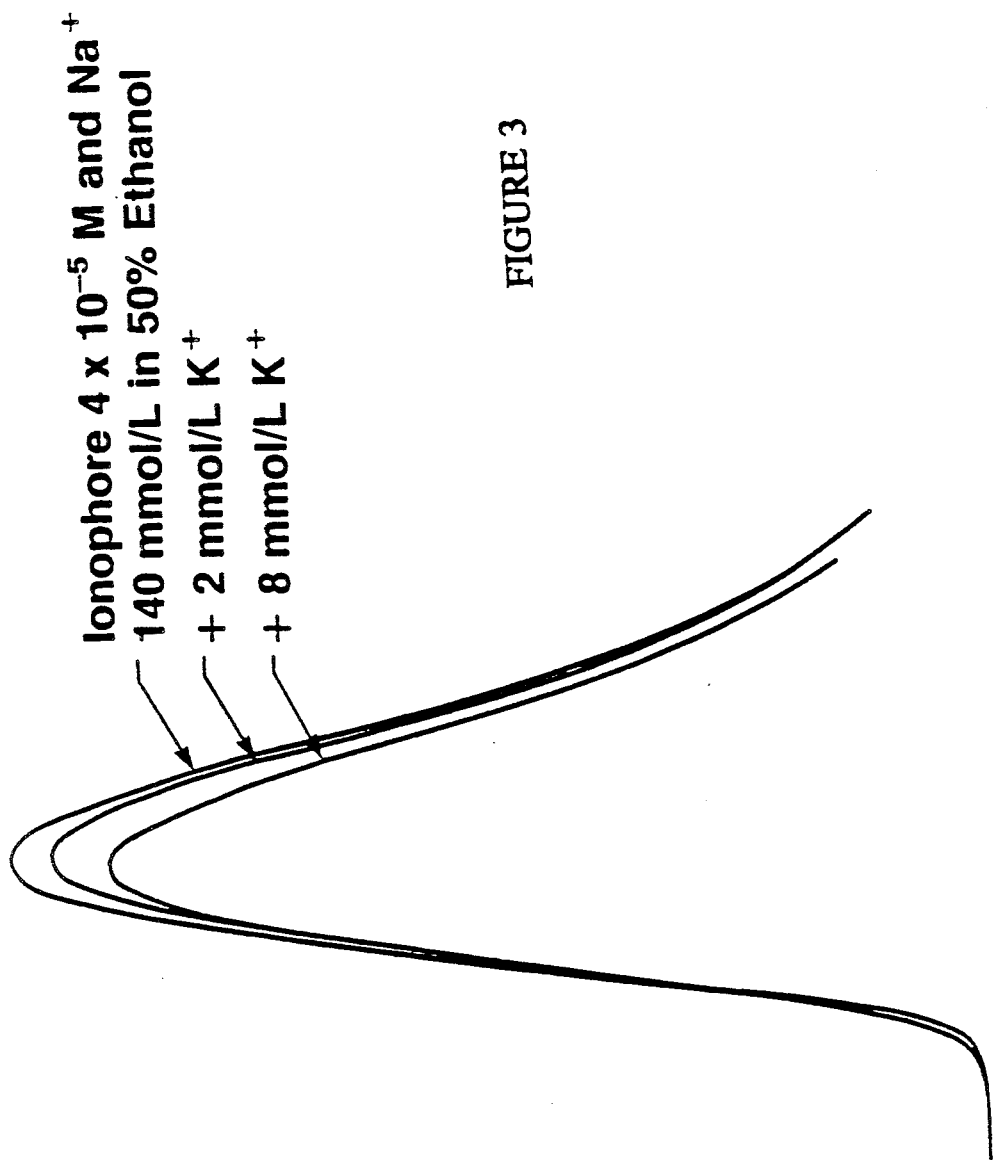
FIG. 3 depicts a graph of fluorescence of 6,7-(4-methyl) coumaro-18-crown-6 bound to different amounts of potassium ion in the presence of serum-like concentration of sodium ion.

The selectivity and sensitivity of 6,7-(4-methyl)-coumaro-18-crown-6 in direct quantitative analysis of potassium ion in human blood is demonstrated in this example. The concentration of potassium ion in human blood serum varies from 3.5–5.3 mmol/L while sodium ion is present in a large excess (135–148 mmol/L). Solutions in 50/50 ethanol/water at neutral pH containing $10^{-5}M$ 6,7-(4-methyl)coumaro-18-crown-6, 160 mmol/L of sodium chloride and varying amounts (0–6.0 mmol/L) of potassium chloride were prepared. The fluorescence emission of these solutions were measured as described in Example 15. FIG. 3 shows that the fluorescence is progressively quenched with increasing amounts of potassium ion thus demonstrating the ability of this ionophore to measure shall changes in potassium ion in the presence of large excess of sodium ion. (Changing the concentration of the sodium ion from 160 mmol/L to 150 mmol/L did not affect the fluoescence emission intensities of the ionophore significantly.) Since the fluorescence intensities are reproducible and are sensitive only to changes in potassium ion concentrations, they can be used reliably in preparing standard charts (fluorescence intensity vs. concentration) for potassium ion. These charts may then be used for determining the level of potassium ion in human serum.

EXAMPLE 17

Selectivity of 6,7(4-methyl)coumaro-21-crown-7 for potassium ion

Figure 4:
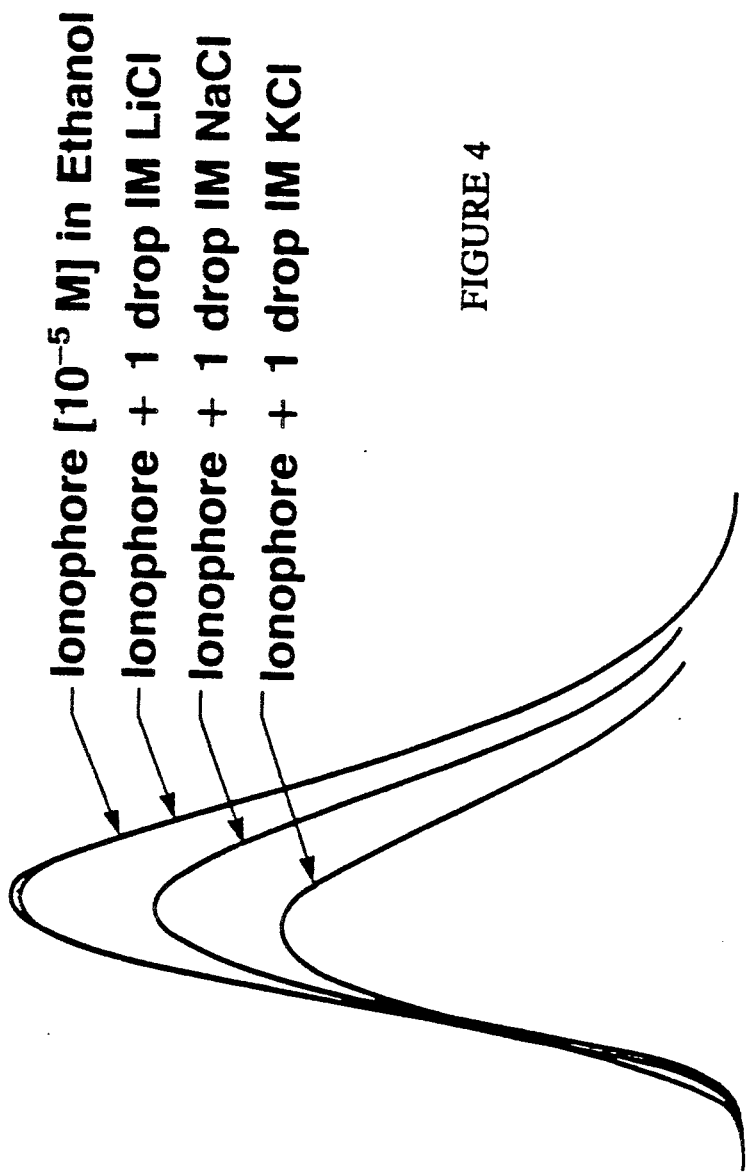
FIG. 4 depicts selective quenching of fluorescence of 6,7-(4-methyl) coumaro-21-crown-7 upon binding with potassium ion.

The experiment described in Example 15 was repeated with a $10^{-5}M$ solution of 6,7-(4-methyl)-coumaro-21-crown-7. As in Example 15, the addition of one drop of 1M potassium chloride showed a dramatic quenching of the fluorescence emission. Sodium ion caused slight quenching while effect of lithium ion was insignificant (see FIG. 4). The experiment demonstrates that the above ionophore is a selective indicator for potassium ion.

EXAMPLE 18

Quantitative analysis of potassium ion in serum-like solutions using 6,7-(4-methyl)coumaro-21-crown-7

The experiment described in Example 16 was repeated using $4 \times 10^{-5}M$ 6,7-(4-methyl)coumaro-21-crown-7 with identical result. As in Example 16, the fluorescence intensities are reproducible and are sensitive only to changes in potassium ion concentrations (see FIG. 5) and hence standard charts (fluorescence intensity vs. potassium ion concentration) can be prepared which can be used for determining the level of potassium ion in human serum samples.

EXAMPLE 19

Selectivity of 6,7-(4-methyl)coumaro-15-crown-5 for sodium ion

Figure 6:
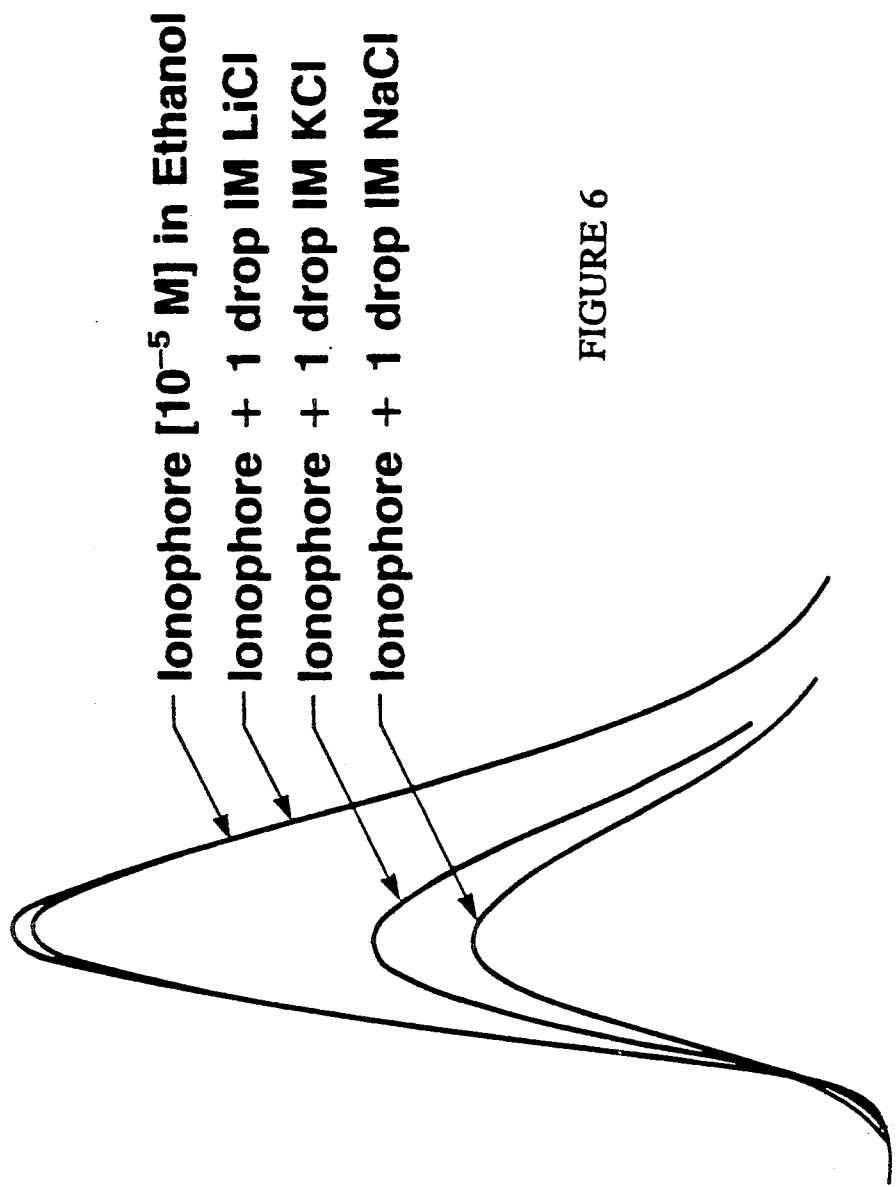
FIG. 6 depicts selective quenching of fluorescence of 6,7-(4-methyl) coumaro-15-crown-5 upon binding with sodium ion.

The experiment described in Example 15 was repeated with a $10^{-5}M$ solution of 6,7-(4-methyl)-coumaro-15-crown-5. However, with this ionophore, dramatic quenching of fluorescence was observed when 1 drop of 1M sodium chloride was added. Fluorescence quenching was less dramatic for 1M potassium chloride. The effect was insignificant for lithium ion. This experiment demonstrates that the ionophore is a selective indicator for sodium ion (see FIG. 6).

EXAMPLE 20

Evaluation of ion detection limits of fluorogenic ionophores

Solutions of fluorogenic ionophores ($10^{-5}$M) in 50/50 ethanol/water containing varying amounts of a given salt (potassium chloride or sodium chloride) were prepared. The relative fluorescence emission (Io/I) of these solutions was plotted against salt concentrations. FIG. 1 shows such a plot for 6,7-(4-methyl)coumaro-18-crown-6 and 6,7-(4-methyl)coumaro-21-crown-7 against potassium chloride and sodium chloride. From FIG. 1, it is clear that quenching is most sensitive to potassium ion concentration from 0–20 mmol/L for both ionophores. The limiting value of fluorescence quenching by potassium ion is around 60 mmol/L for 6,7-(4-methyl)coumaro-18-crown-6 while it is around 100 mmol/L for the 21-crown-7 system. Even though the 18-crown-6 system is more sensitive to potassium ion than the 21-crown-7 system, the former also shows a significant quenching of fluorescence by sodium ion. The effect of sodium ion on fluorescence in the 21-crown-7 system is not significant. Thus, the 21-crown-7 appears to be more selective for potassium ion over sodium ion though less sensitive than the 18-crown-6 system.

EXAMPLE 21

Compatibility of fluorogenic ionophores in aqueous medium

The experiments described above (Examples 15, 17, 19) were repeated in aqueous (or 50/50 ethanol/water) medium. The fluorescence intensities were of the same order. Thus the ionophores developed are compatible with aqueous, alcoholic or mixtures of water and alcohol media.

EXAMPLE 22

Intramolecular quenching in 2,3-Naphtho-18-crown-6 with ligating side arm carrying a quenching group The intramolecular fluorescence quenching of 11-(m-dinitrobenzoyloxymethyl)-2,3-naphtho-18-crown-6 was demonstrated as follows: First the fluorescence emission of 11-benzyloxymethyl-2,3-naphtho-18-crown-6 ($10^{-4}$M) in dioxane was recorded. (The ligating side arm in this compound does not carry a quenching group.) On adding an external quenching compound, namely 2-methoxyethyl-m-dinitrobenzoate in incremental amounts the fluorescence was quenched to an extent of 72% at $10^{-4}$M concentration of the quencher (see FIG. 7). 11-(m-Dinitrobenzoyloxymethyl)-2,3-naphtho-18-crown-6 (Structure 18) ($10^{-5}$M in dioxane) shows very weak fluorescence (FIG. 8b) due to efficient intramolecular quenching by the m-dinitrobenzyl group at the terminus of the side arm. Without the quenching group, a $10^{-5}$M solution of 11-benzyloxymethyl-2,3-naphtho-18-crown-6 in dioxane shows significant fluorescence emission due to its naphthalene group (see FIG. 8a).

Fluorescence Spectra of Preferred Reagents

The fluorescence excitation spectra of the compounds show close similarity to their absorption spectra. Fluorescence measurements were carried out in a neutral 50/50 ethanol/water medium using exciting wavelength of 330 nm and scanning emission wavelengths between 340–540 nm, giving a broad peak with a maximum at 410 nm. Addition of metal ions to the solution did not change the UV spectrum. However, selective quenching of fluroescence was observed when the metal ion with the best "fit" in the ionophore cavity was added. Thus, 6,7-(4-methyl) coumaro-18-crown-6 (Structure 15), with its ionophore cavity ideally suited for accommodating potassium ion, showed a dramatic quenching of fluorescence for this ion. Some quenching was observed for sodium ion. Lithium ion showed very little change in fluorescence intensity. (See FIGS. 1 and 2). In human blood serum, the level of sodium is high (135–148 mmol/L) while that for potassium ion ranges from 3.5–5.3 mmol/L. FIG. 3 shows that 6,7-(4-methyl) coumaro-18-crown-6 can quantitatively measure changes in the concentration of the potassium ion ranging from 2 to 8 mmol/L in the presence of 140 mmol/L of sodium ion at neutral pH. The ionophore could therefore be ideally suited for a fluoescence-based sensor for the direct monitoring of potassium ion in blood serum and other biological fluids. It should be noted that there is no kinetic barrier to complex formation between the ionophores and metal ions. The equilibrium is established rapidly, and thus, continuous monitoring is made possible.

Figure 5:
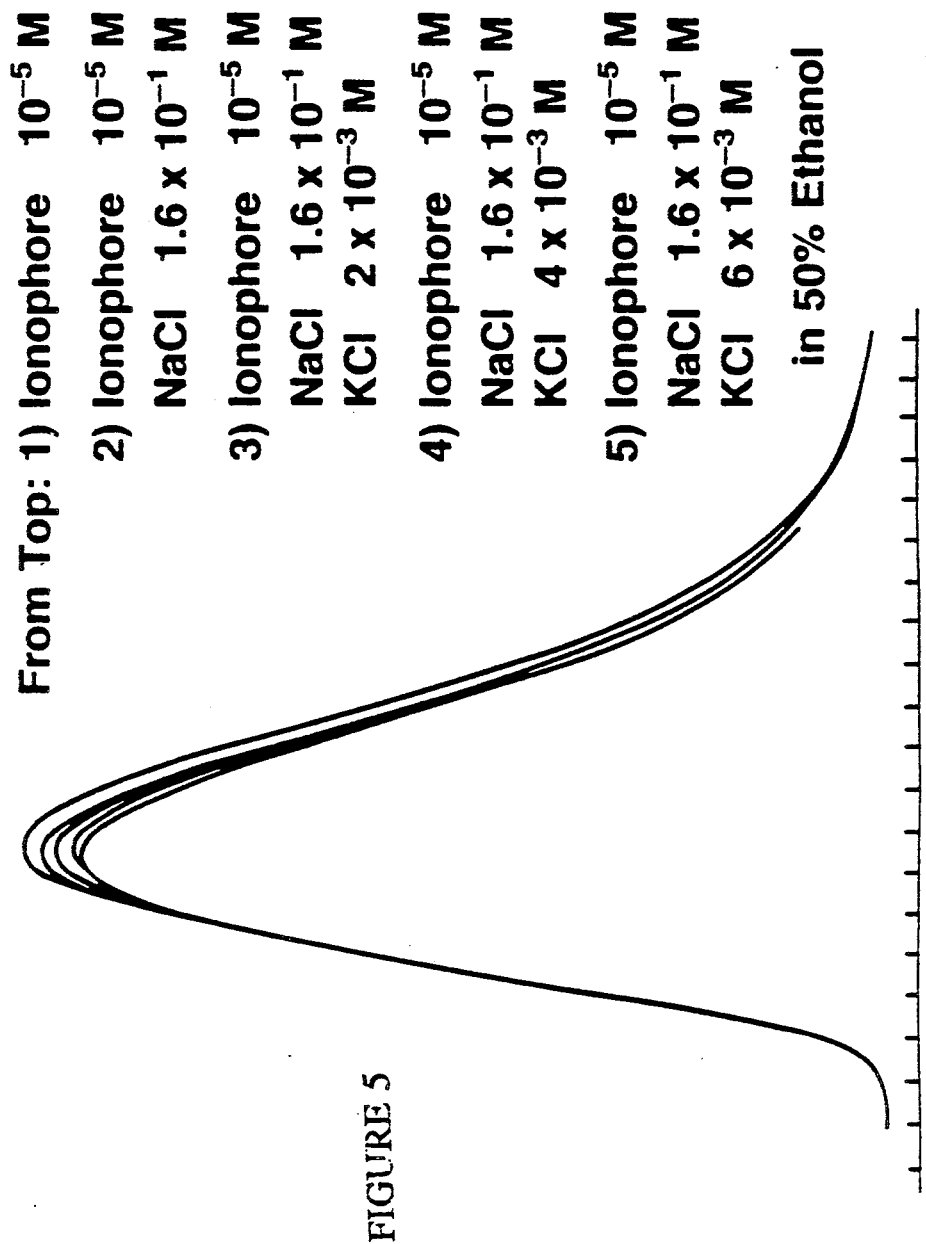
FIG. 5 depicts a graph of fluorescence of 6,7-(4-methyl) coumaro-21-crown-7 bound to different amounts of potassium ion in the presence of serum-like concentration of sodium ion.

The ionophore cavity in 6,7-(4-methyl) coumaro-21-crown-7 (Structure 16) is too large for potassium ion and more so for sodium ion. A selective quenching of fluorescence by potassium ion (compared to sodium ion) was observed for this ionophore (see FIGS. 1 and 4) even though its sensitivity was not as high. FIG. 5 shows that 6,7-(4-methyl) coumaro-21-crown-7 can quantitatively measure concentration changes of potassium ion ranging from 2 to 6 mmol/L in the presence of 160 mmol/L of sodium ion at neutral pH (mimicking potassium and sodium ions in human blood serum).

The 6,7-(4-methyl) coumaro-15-crown-5 (Structure 17) shows a selective quenching of fluorescence for sodium ion. The quenching by potassium ion is less dramatic and lithium ion shows very little change in fluorescence (see FIG. 6.) This ionophore is therefore exemplary of those suited for the quantitative determination of sodium ion in biological samples.

Figure 7:
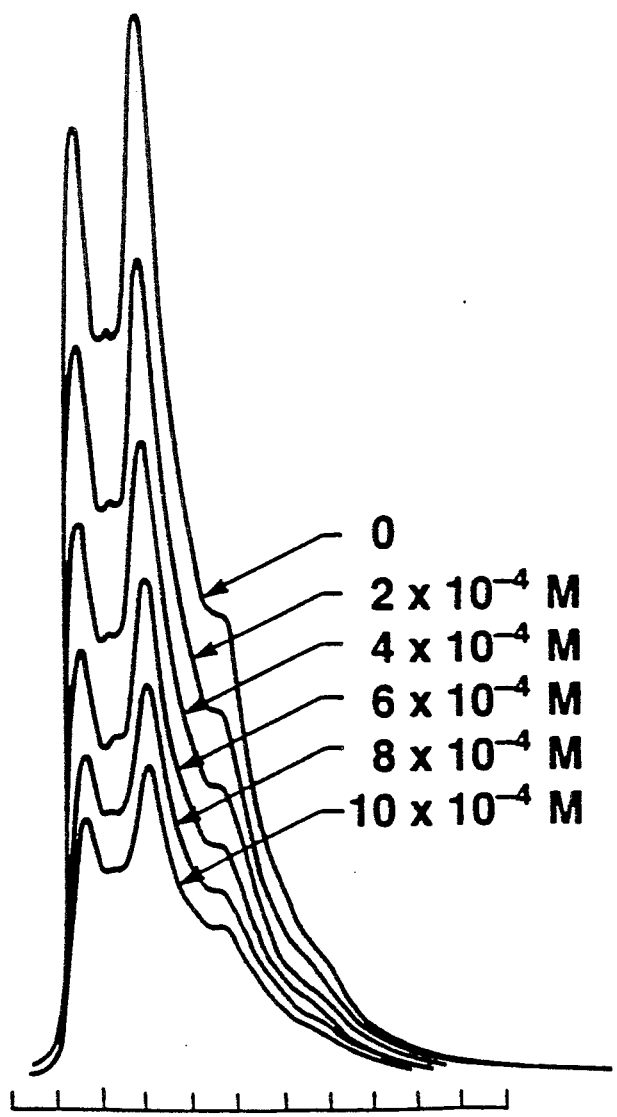
FIG. 7 shows the effect of adding on external quencher (2-methoxyethyl-m-dinitrobenzoate) on the fluorescence emission of 11-benzyloxymethyl-2,3-naphtho-18-crown-6.

In the case of 2,3-naphtho crown ethers, fluroescence measurements were carried out in dioxane using exciting wavelength of 309 nm and scanning emission wavelengths between 320–420 nm giving a broad peak with two maxima at 328 nm and 348 nm. FIG. 7 shows the fluorescence spectrum of 11-benzyloxymethy-2,3-naphtho-18-crown-6 at $10^{-4}$M in dioxane. In adding 2-methoxyethyl-m-dinitrobenzoate as an external quencher in incremental amounts, it was found that fluorescence was quenched to an extent of 72% at $10^{-3}$M concentration of the quencher. In the case of naphthocrown ether with ligating side arm bearing a m-dinitrobenzoate quenching group, the intra-molecular quenching, as anticipated, was very efficient. Thus, in a $10^{-5}$M solution of 11-(m-dinitrobenzoyloxymethyl)-2,3-naphtho-18-crown-6 (Structure 18) in dioxane, very weak fluorescence emission (see FIG. 8b) was noted. On adding metal ions, an enhancement of the fluorescence emission is expected, since the metal ion will separate the quenching group away from the fluorescing naphthalene functionality. Similar results are anticipated for a N-(m-dinitrobenzyoyloxyethyl)-2,3-naphtho-10-aza-15-crown-5 system also.

What is claimed is:

1. An ionophore compound of an ion-recognizing system fused to a signal moiety through two heteroatoms having a non-bonded electron pair, having the formula:

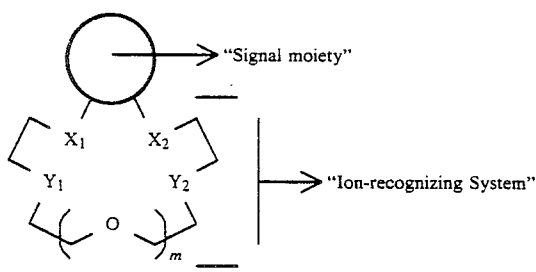

wherein said signal moiety is selected from the group consisting of unsubstituted and substituted coumarins, and wherein said ion-recognizing system is a crown ether wherein $X_1$ and $X_2$ of said crown ether are the same or different and are selected from the group consisting of S, P, N, O, and Se, $Y_1$ and $Y_2$ are the same or different and are selected from the group consisting of O, N, S, and C; and wherein the repeating unit m is 0 to 12.

2. The ionophore of claim 1 wherein $X_1$ and $X_2$ are the same or different and are selected from the group consisting of S, O and N.

3. The ionophore compound of claim 1 wherein $X_1$ and $X_2$ are the same and are O or N.

4. The ionophore compound of claim 3 wherein m is 0 to 3.

5. The ionophore compound of claim 4 wherein m is 0 or 1.

6. The ionophore compound of claim 1 wherein the ionophore compound corresponds to a formula selected from the group consisting of:

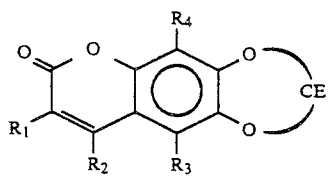

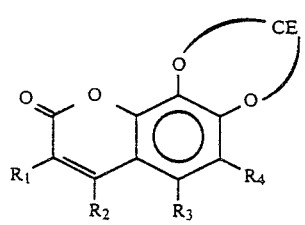

wherein $R_1$, $R_2$, $R_3$ and $R_4$ are the same or different and are H, hydroxyl, amino, alkyl, aromatic hydrocarbyl, fluoroalkyl, alkylcarbonyloxyl, carboxyl, alkoxyl, mercapto or alkylthio and CE represents a crown ether.

7. A compound having the following formula:

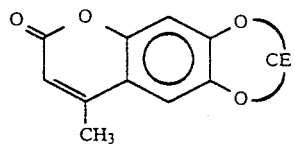

wherein CE is a crown ether.

8. The compound of claim 6 wherein $R_1$, $R_2$, $R_3$ and $R_4$ are the same or different and are selected from H and alkyl having 1 to 4 carbons.

9. The compound of claim 6 wherein $R_1$, $R_2$, $R_3$ and $R_4$ are the same or different and are selected from H or methyl or ethyl.

10. A compound according to claim 7 having the formula:

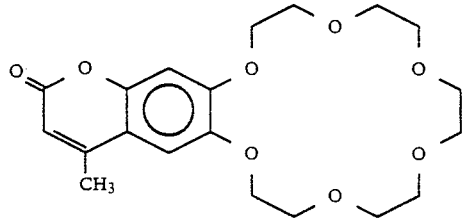

wherein said compound is a fluorogenic reagent selective for the detection of potassium ion.

11. A compound according to claim 7 having the formula:

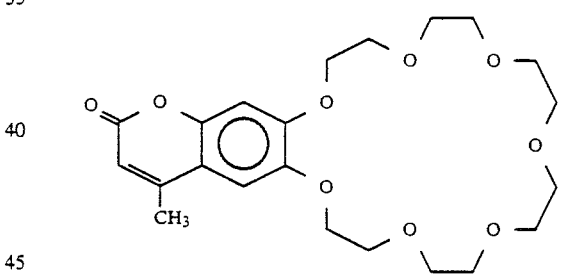

wherein said compound is a fluorogenic reagent selective for the detection of potassium ion.

12. A compound according to claim 7 having the formula:

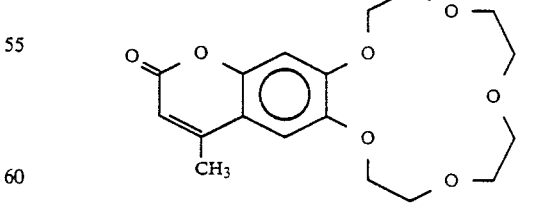

wherein said compound is a fluorogenic reagent for the detection of sodium ion.

13. An ionophore compound comprising an ion-recognizing system fused to a signal moiety through two heteroatoms having a non-bonded electron pair, having the formula:

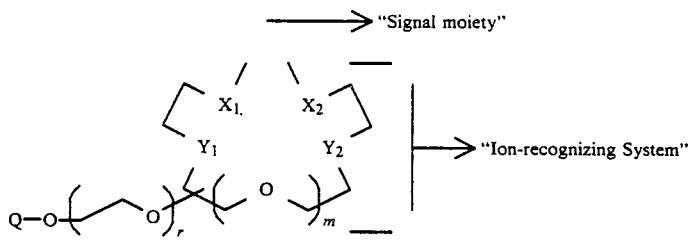

wherein said signal moiety is selected from the group consisting of unsubstituted and substituted coumarins, and wherein said ion-recognizing system is a crown ether, wherein $X_1$, and $X_2$ of said crown ether are the same or different and are selected from the group consisting of S, P, N, O, and Se, $Y_1$ and $Y_2$ are the same or different and are selected from the group consisting of O, N, S, and C; and wherein the repeating unit m is 0 to 12; and wherein r ranges from 0–15 and Q is a quenching group selected from aceto, propionyl, bromoaceto, chloroaceto, benzoyl, dinitrobenzoyl, methylcarbonyl, phenylcarbonyl and cyclohexylcarbonyl.

14. The ionophore of claim 1 wherein said ionophore is capable of selectively recognizing a Na, K or Li ion.

* * * * *